United States Patent
Passerini et al.

(10) Patent No.: US 11,605,447 B2
(45) Date of Patent: Mar. 14, 2023

(54) INTELLIGENT AGENTS FOR PATIENT MANAGEMENT

(71) Applicant: Siemens Healthcare GmbH, Erlangen (DE)

(72) Inventors: Tiziano Passerini, Plainsboro, NJ (US); Puneet Sharma, Monmouth Junction, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 363 days.

(21) Appl. No.: 15/795,673

(22) Filed: Oct. 27, 2017

(65) Prior Publication Data

US 2019/0130067 A1 May 2, 2019

(51) Int. Cl.
*G16H 10/60* (2018.01)
*G16H 50/20* (2018.01)
*G16H 30/40* (2018.01)
*G06Q 10/06* (2023.01)
*G16H 40/20* (2018.01)

(52) U.S. Cl.
CPC ........... *G16H 10/60* (2018.01); *G16H 30/40* (2018.01); *G16H 50/20* (2018.01); *A61M 2205/502* (2013.01); *G06Q 10/06* (2013.01); *G16H 40/20* (2018.01)

(58) Field of Classification Search
None
See application file for complete search history.

(56) References Cited

U.S. PATENT DOCUMENTS

| | | | |
|---|---|---|---|
| 9,349,178 B1 | 5/2016 | Itu et al. | |
| 2005/0020903 A1* | 1/2005 | Krishnan | G16H 50/20 600/407 |
| 2007/0112876 A1* | 5/2007 | Blaisdell | G06F 16/254 |
| 2007/0118399 A1* | 5/2007 | Avinash | G06F 19/328 705/2 |
| 2011/0295621 A1* | 12/2011 | Farooq | G06Q 10/10 705/3 |
| 2012/0124022 A1* | 5/2012 | Goping | G16H 50/20 707/705 |

(Continued)

OTHER PUBLICATIONS

Montalescot, "2013 ESC guidelines on the management of stable coronary artery disease" (2013), European Heart Journal (2013) 34, 2949-3003 (Year: 2013).*

(Continued)

*Primary Examiner* — Shahid Merchant
*Assistant Examiner* — Andrew E Lee (57) ABSTRACT

A computer-implemented method for executing patient management workflows includes acquiring a pre-test dataset of clinically relevant information related to a patient and using a first intelligent agent to identify a diagnostic test for the patient based on the pre-test dataset. Following performance of the diagnostic test, a second intelligent agent is used to select a processing technique to be applied to data collected from the diagnostic test to obtain a diagnostic marker. Following application of the processing technique to the data collected from the diagnostic test, a third intelligent agent is used to generate an optimal patient management plan based on the pre-test dataset, the data collected from the diagnostic test, and the diagnostic marker.

15 Claims, 4 Drawing Sheets

(56) References Cited

U.S. PATENT DOCUMENTS

| | | | | |
|---|---|---|---|---|
| 2013/0024213 | A1* | 1/2013 | Poon | A61B 6/56 705/3 |
| 2013/0132054 | A1 | 5/2013 | Sharma et al. | |
| 2014/0058715 | A1 | 2/2014 | Sharma et al. | |
| 2015/0164342 | A1* | 6/2015 | Choi | A61B 5/02007 600/407 |
| 2016/0180222 | A1* | 6/2016 | Sierhuis | G06F 7/023 706/47 |
| 2016/0239956 | A1* | 8/2016 | Kang | A61B 6/032 |
| 2017/0032097 | A1 | 2/2017 | Itu et al. | |
| 2017/0132388 | A1* | 5/2017 | Grady | G16H 50/50 |
| 2017/0245821 | A1 | 8/2017 | Itu et al. | |
| 2017/0296055 | A1* | 10/2017 | Gardner | G06F 16/254 |
| 2018/0089385 | A1* | 3/2018 | Gupta | G16H 50/20 |
| 2018/0107800 | A1* | 4/2018 | Cerrone | G16H 80/00 |
| 2018/0144465 | A1* | 5/2018 | Hsieh | A61B 6/032 |
| 2018/0144466 | A1* | 5/2018 | Hsieh | G16H 50/20 707/705 |

OTHER PUBLICATIONS

Argall, Brenna D., et al. "A survey of robot learning from demonstration." Robotics and autonomous systems 57.5 (2009): 469-483.

Bengio, Y., et al. 2009. Curriculum learning. In ICML.

K. Sycara et al. "Distributed Intelligent Agents," IEEE Expert, Dec. 1996.

K. Sycara Multiagent Systems, AI Magazine, vol. 9, No. 2, p. 79-92, 1998.

R.S. Sutton, A.G. Barto, Reinforcement learning: an introduction, The MIT Press, Cambridge, MA, London, England, 1998.

Jennings, N., et al. 1998. A Roadmap for Agent Research and Development. Autonomous Agents and Multiagent Systems 1(1): 7-38.

Dominik Neumann, et al., "A Self-Taught Artificial Agent for Multi-Physics Computational Model Personalization", to appear on Medical Image Analysis, 2016.

Sharma P, et al. A framework for personalization of coronary flow computations during rest and hyperemia. In Engineering in Medicine and Biology Society (EMBC), 2012 Annual International Conference of the IEEE, 6665-6668, IEEE, 2012.

* cited by examiner

INTELLIGENT AGENTS FOR PATIENT MANAGEMENT

TECHNICAL FIELD

The present invention relates generally to methods, systems, and apparatuses associated with using intelligent agents for patient management. The disclosed methods, systems, and apparatuses may be applied to scanners for any imaging modality.

BACKGROUND

Healthcare is steadily moving from a fee-for-service paradigm to a fee-for-value paradigm. This reflects in a growing pressure on healthcare providers to streamline workflows with the goal of containing the cost and improving patient outcomes. In this context, a major challenge is deciding how to stratify patients based on imaging and medical data. Another challenge in this context is deciding how to select the best therapy for a patient based on imaging and medical data. These challenges call for new tools that can assist healthcare professionals to systematically determine the best option in patient management, guaranteeing objective and standardized quality of care.

Figure 1:
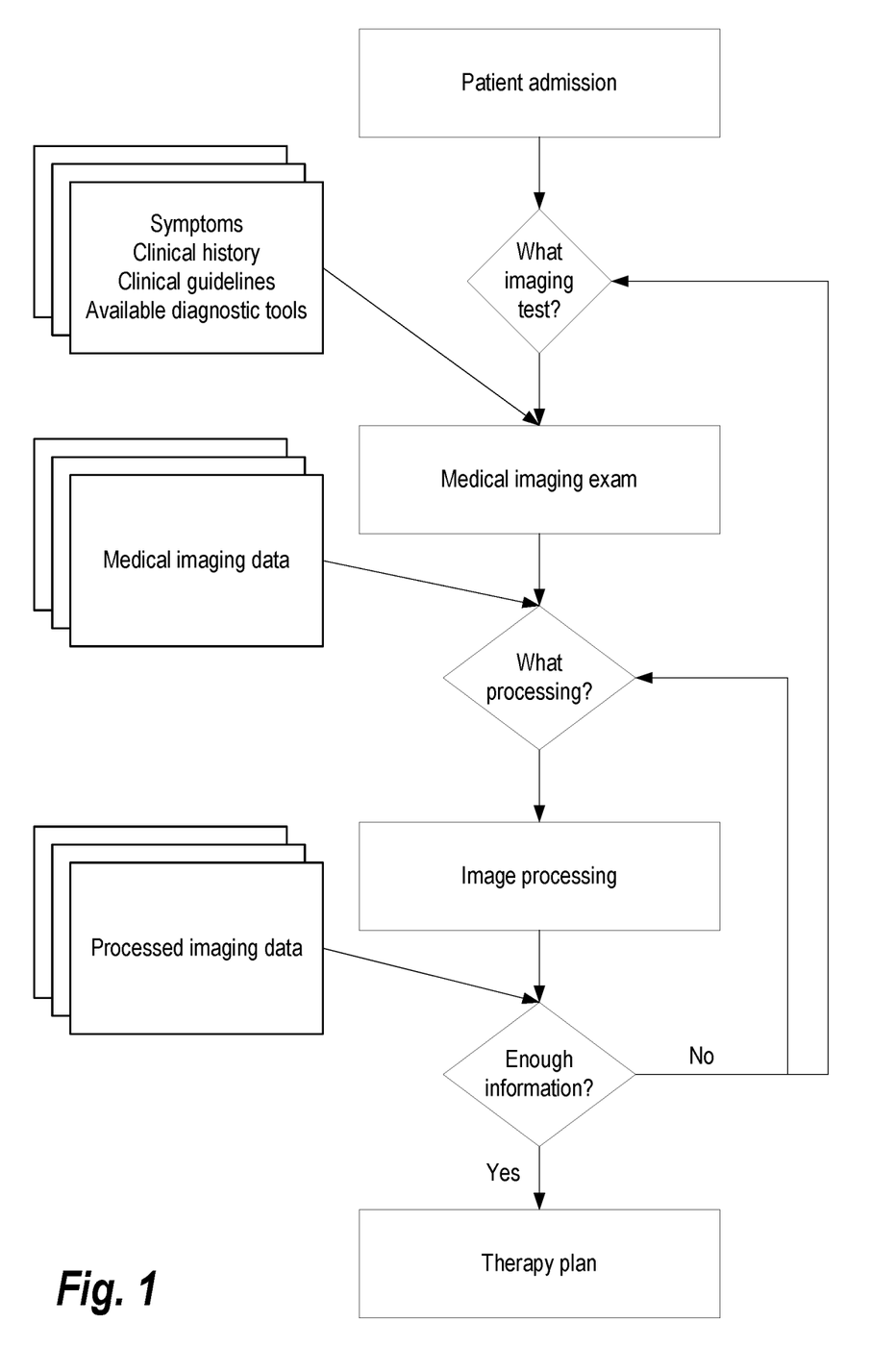
FIG. 1 illustrates an example patient management workflow.

Patient management is typically implemented in a staged workflow, from patient admission to definition and delivery of a therapy plan. To illustrate an example, we focus without loss of generality on a patient management plan requiring medical imaging data. The corresponding workflow can be represented in FIG. 1. At each step of the procedure, available information has to be analyzed to identify the optimal course of action. Each of these decision points requires the integration of heterogeneous data and the ability to select the best available tool for the following step. The choice has to follow criteria of therapeutic efficacy as well as workflow efficiency, to maximize outcome for the specific patient and performance of the entire healthcare system. With conventional technology, the design of the optimal patient management plan is left to the clinician, and no tool is available that supports the integration of heterogeneous data and selection of the best available tool for each step in the clinical workflow.

SUMMARY

Embodiments of the present invention address and overcome one or more of the above shortcomings and drawbacks, by providing methods, systems, and apparatuses related to the use of intelligent agents for patient management. Briefly, a multi-agent system is employed where multiple intelligent agents are employed to perform a patient management workflow. Each intelligent agent is responsible for a decision point in the patient management workflow. More specifically, at each step of the workflow, an intelligent agent uses machine learning principles to integrate and analyze available data and propose actions for the next step in the workflow.

According to some embodiments, a computer-implemented method for executing patient management workflows includes acquiring a pre-test dataset of clinically relevant information related to a patient and using a first intelligent agent to identify a diagnostic test for the patient based on the pre-test dataset. Following performance of the diagnostic test, a second intelligent agent is used to select a processing technique to be applied to data collected from the diagnostic test to obtain a diagnostic marker. Following application of the processing technique to the data collected from the diagnostic test, a third intelligent agent is used to generate an optimal patient management plan based on the pre-test dataset, the data collected from the diagnostic test, and the diagnostic marker. This patient management plan may include, for example, patient logistics information corresponding to a medical facility.

Various enhancements, refinements, and other modifications may be made to the method discussed above. For example, in some embodiments, the pre-test dataset of clinically relevant information related to the patient is automatically extracted from the one or more electronic medical records to yield the pre-test dataset. In other embodiments, patient data corresponding to a plurality of patients from a common knowledge database, and the second intelligent agent selects the processing technique to be applied to data collected from the diagnostic test based on the patient data. In other embodiments, the third intelligent agent generates the optimal patient management plan based on the pre-test dataset, the data collected from the diagnostic test, the diagnostic marker, and the patient data. Additionally, in some embodiments, the third intelligent agent to generate an optimal drug therapy plan based on the pre-test dataset, the data collected from the diagnostic test, and the diagnostic marker.

As an example implementation of the aforementioned method, in one embodiment, the diagnostic test is a diagnostic imaging test and the processing technique is an image processing technique. The first intelligent agent may be used to identify an optimal imaging protocol for performing the diagnostic imaging test. The imaging processing technique may include, for example, one or more of segmentation of a vascular tree, detection of vascular lesions, classification of detected lesions into clinical sub-types, or extraction of geometry features for physiological modeling.

According to another aspect of the present invention, a system for executing patient management workflows includes a common knowledge database and a plurality of intelligent agents. The common knowledge database stores clinically relevant information related to a population of patients. The first intelligent agent is configured to identify a diagnostic test for the patient based on one or more of (a) a pre-test dataset of clinically relevant information related to a patient and (b) the clinically relevant information. The second intelligent agent is configured to select a processing technique to be applied to data collected from the diagnostic test to obtain a diagnostic marker based on one or more of (a) the pre-test dataset and (b) the clinically relevant information. The third intelligent agent is configured to generate an optimal patient management plan based on one or more of (a) the pre-test dataset, (b) the clinically relevant information, (c) the data collected from the diagnostic test, and (d) the diagnostic marker. In some embodiments, the functionality of the three intelligent agents may be combined into one or two agents rather than using three intelligent agents as discussed above. Similarly, in other embodiments, the functionality may be split among more than three intelligent agents. In one embodiment, the system further includes a graphical user interface (GUI) configured to present the optimal patient management plan.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

Systems, methods, and apparatuses are described herein which relate generally to various techniques related to the use of intelligent agent for patient management. More specifically, the technology described herein employs a system of intelligent agents, each responsible for a decision point in the patient management workflow. The role of the intelligent agent is integrating and analyzing the available information; and proposing an action for the next step in the workflow. The decision is based on patient-specific information as well as contextual information (e.g., clinical guidelines, medical literature) and practical constraints (e.g., the availability of diagnostic tools). Additionally, each intelligent agent can have access to a common knowledge database where patient data is stored. Each patient dataset in the common knowledge database may include, for example, a description of what management plan was followed, and the corresponding outcome. Moreover, in some embodiments, the common knowledge database is continuously updated with data for each processed patient. Patient information in the database may be anonymized in some embodiments such that it does not include any personally identifiable information.

Figure 2:
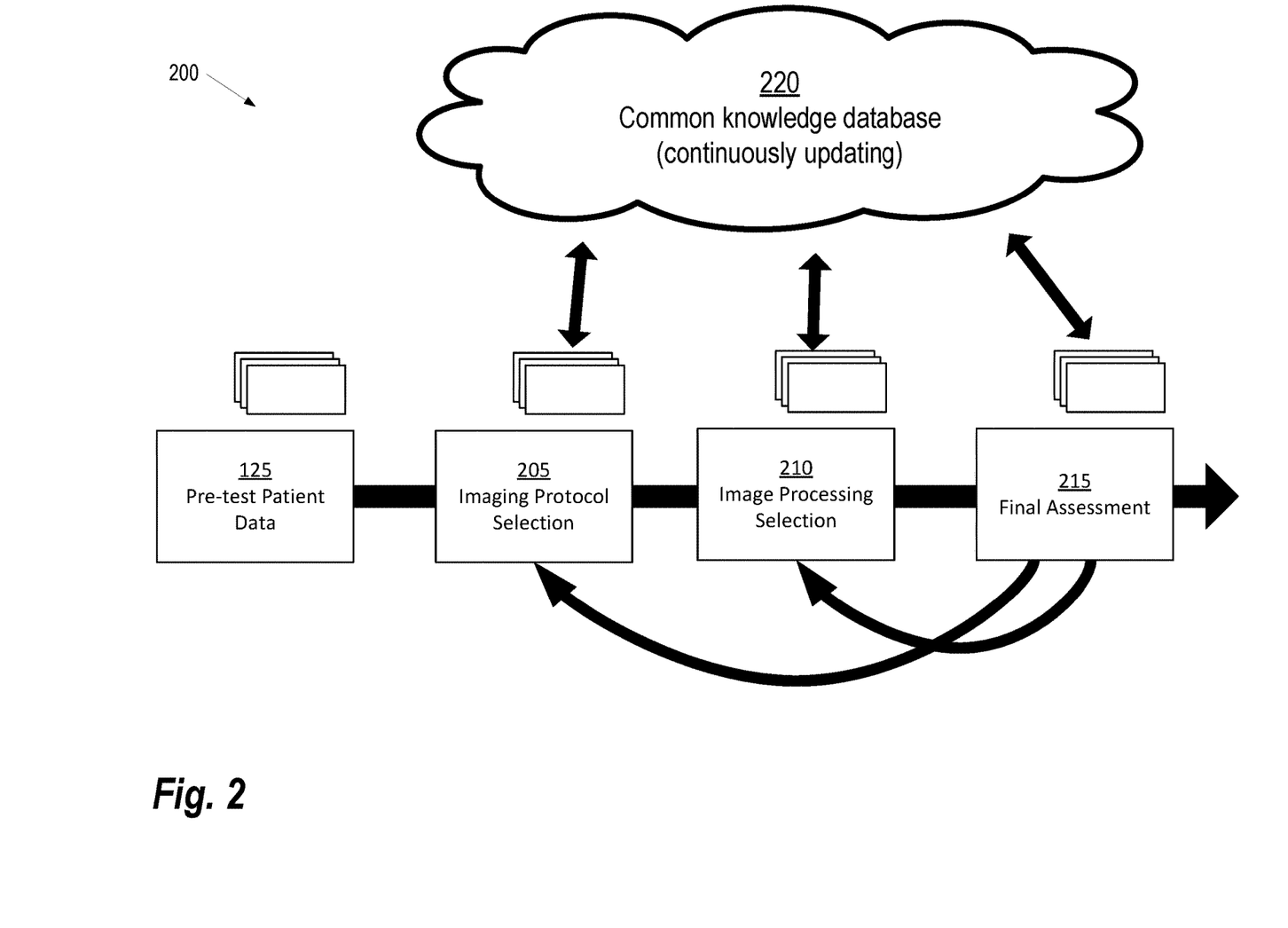
FIG. 2 shows a graphical representation of a multi-agent system configured to perform patient management operations, according to some embodiments.

FIG. 2 shows a graphical representation of a multi-agent system 200 configured to perform patient management operations, according to some embodiments. This example illustrates the design of a medical management plan based on diagnostic imaging. However, it should be under that the multi-agent system 200, and the other techniques described herein, may be readily adopted for other types of diagnostic testing (e.g., non-imaging stress testing).

Multi-agent systems are designed to tackle problems that are complex, large or unpredictable (i.e., they can dynamically change). They can out-perform centralized single agents which could be limited in terms of resources or act as bottlenecks for the access to data. They naturally adapt to situations where data and expertise are distributed, and offer the benefits typical of a modular system (computational efficiency, reliability thanks to redundancy, extensibility, robustness, maintainability, flexibility). Additionally, in the context of diagnostics testing, the use of multiple agents (as opposed to a single agent or unitary process) offers a level of transparency that may be important for medical scenarios. Rather than adopting a "black box" approach that performs diagnostics automatically based on a set of inputs, a multi-agent approach separates diagnostic testing into a plurality of steps and the results of each step can be reviewed, verified, and validated.

In the example of FIG. 2, the multi-agent system 200 comprises a collaborative, distributed collection of three Intelligent Agents 205, 210, and 215. An intelligent agent is an autonomous software entity capable of making decisions based on a set of inputs and experience processing similar inputs received in the past. The "intelligence" of the agent comes from the use of artificial intelligence to direct the intelligent agent's operations toward achieving one or more goals. Intelligent agents can be implemented using various machine learning models and related algorithms generally known in the art. Examples of such machine learning models include deep neural networks and convolutional neural networks.

The initial input into the multi-agent system 200 is Pre-test Patient Data 125. In general, the Pre-test Patient Data 125 includes any patient information that may be relevant to performing diagnostic tests. Thus, it may include information such as patient demographics, symptoms, family history, clinical history, or any other available medical data. In some embodiments, a graphical user interface (GUI) or other interface may be used to collect the pre-test data. For example, in some embodiments, this pre-test interface comprises software that retrieves the pre-test data through interaction with users or communicating with patient intake systems or other systems storing patient data (e.g., as Electronic Medical Records).

Common Knowledge Database 220 stores patient data such as patient symptoms, clinical history, medical data, medical imaging, background knowledge from medical literature, clinical guidelines, appropriate use criteria, etc. In some embodiments, all data in the Common Knowledge Database 220 is anonymized to remove any personally identifying information associated with the patients. In some embodiments, the Common Knowledge Database 220 is shared among different multi-agent systems, so that it always contains a mixture of previously seen and unseen data.

In the example of FIG. 2, the Intelligent Agents 205, 210, and 215 correspond to the goals of imaging protocol selection, image processing method selection, and final assessment, respectively. Thus, using the Pre-test Patient Data 125 and the Common Knowledge Database 220, the diagnostic technique described above with respect to FIG. 1 is automated and enhanced by integrating heterogeneous data and selecting the best available tool for each step in the clinical workflow. At any point in the workflow shown in FIG. 2, a human user could overrule an intelligent agent's decision or guide/edit the intelligent agent's actions (e.g., by confirming/rejecting the agent's choices at every stage of the workflow). An example process for using the Intelligent Agents 205, 210, and 215 is described below with respect to FIG. 3.

Various techniques may be used for training and optimizing the behavior of the multi-agent system 200. For example in some embodiments, each agent is trained independently to optimize the execution of the specific task. However, this approach has the potential disadvantage of making the learning process overall more difficult for the multi-agent system, since the environment effectively changes as each agent learns. As an alternative approach, learning can be integrated into a negotiation process that guarantees the maximization of the overall (joint) system utility.

Each of the Intelligent Agents 205, 210, and 215 performs actions based on available data: this is a well-known problem in the context of robotics applications, and it is typically recast into the problem of learning policies (i.e., the mapping between world states and actions). Different strategies for policy learning by intelligent agents are generally known in the art, including learning by experience (e.g., reinforcement learning) and learning from demonstration ("LfD"). In the context of this system 200 and the techniques described herein, learning from demonstration could be implemented with a human expert executing an intelligent agent's task for one or more example cases, thus providing the "ground truth" solution. This would allow the intelligent agent to capture the experts' knowledge. Another possible approach could be for the agent to run virtual clinical scenarios (e.g., provided by a generative model) and gather the experts' knowledge as ground truth by recording the choices that interviewed physicians would implement in the given scenario.

Recent trends suggest that deep learning architectures could have a performance advantage in learning complex tasks, at the price of requiring more difficult training strategies. Curriculum learning could potentially be beneficial in this context, by applying to the network a sequence of training criteria with increasing complexity. In the context of the multi-agent system 200 and the techniques described herein, curriculum training could be applied by having each of the Intelligent Agents 205, 210, and 215 first learn the set of actions maximizing a global measurement of positive outcome for the patient (e.g., irrespective of cost and time efficiency). The, each of the Each of the Intelligent Agents 205, 210, and 215 then learning actions that optimize a more complex objective (e.g., including time- and cost-efficiency, likelihood of further hospitalization, etc.)

Information from the Common Knowledge Database 220 could also be used to continuously train the intelligent agent by retrospectively analyzing large databases of patient-specific medical data and the corresponding outcomes or clinical history of the patients. Using the Common Knowledge Database 220, each intelligent agent could learn information such as what kind of management plan was implemented or what actions led to optimal result (e.g., in terms of outcome, time- or cost-efficiency). In simulated clinical studies, each intelligent agent could learn what different management plans would have a better performance (e.g., different imaging protocols that are more time- or cost-efficient but provide diagnostic information with the same level of accuracy), given the available clinical question and data In some embodiments, the multi-agent system 200 can be tailored to work under specific constraints. For instance, some imaging devices or drugs may not be available in some regions of the world (or in some clinical centers), in which case the system would propose alternative solutions to define the patient's management plan.

Figure 3:
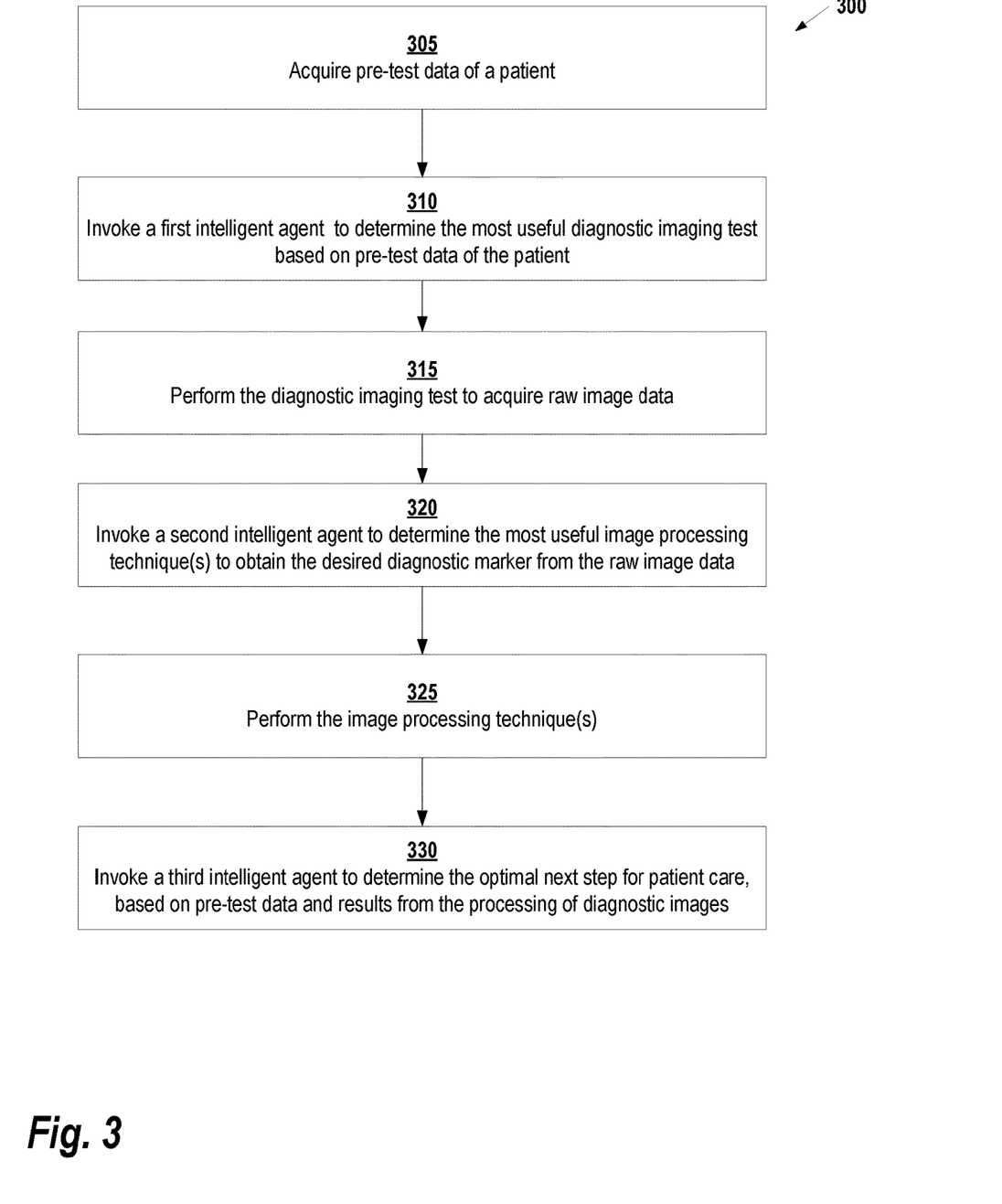
FIG. 3 shows a method for using intelligent agents, according to some embodiments.

FIG. 3 shows a method 300 for using intelligent agents, according to some embodiments. This method may be performed by one or more computing systems. Where multiple computing systems are employed, they may be coupled together via one or more agents. For example, as described below, three different intelligent agents are invoked by steps of the method 300. In one embodiment, each of these intelligent agents comprise an executable application located on a distinct computing system and the agents communication with one another using an application programming interface (API) over a network such as the Internet.

Starting at 305, pre-test data of a patient is acquired by the computing system. This pre-test data may include, for example, patient symptoms, clinical history, available medical data, and/or medical imaging datasets. In some embodiments, the computing system either receives or retrieves one or more electronic medical records (EMRs) which include the pre-test patient data. The computing system then parses the EMRs and extracts the pre-test patient data using any suitable parsing and extraction techniques generally known in the art. In some embodiments, the pre-test patient data also includes one or more previously acquired medical imaging datasets (e.g., functional or structural magnetic resonance imaging datasets).

Next, at step 310, a first intelligent agent is invoked to determine the most useful diagnostic imaging test given the available data and background knowledge from the pre-test data and data in the Common Knowledge Database 220 (e.g., medical literature, clinical guidelines, appropriate use criteria, etc.). Along with identifying the test itself, the first intelligent agent may specify one or more diagnostic markers that should be obtained. Additional details of performing the diagnostic imaging test may also be derived by the first intelligent agent. For example, in some embodiments, the first intelligent agent may determine the optimal imaging protocol for performing the diagnostic imaging test.

Once the diagnostic imaging test is identified, the test is performed at step 315 to acquire raw imaging data. At step 320, a second intelligent agent is invoked to identify the most useful image processing technique(s) to obtain the desired diagnostic marker from the raw image data. Examples of imaging processing techniques that may be identified at step 320 include segmentation of a vascular tree, detection of vascular lesions, extraction of geometry features for physiological modeling, etc. Once the imaging processing technique(s) are identified, they are automatically performed at step 325.

Continuing with reference to FIG. 3, at step 330, a third intelligent agent is invoked to determine the optimal next step for patient care, based on pre-test data and results from the processing of diagnostic images. In some embodiments, the next step may include invoking one or more of the other agents if further tests are required. In other embodiments, the next step may be to design a therapy plan. In one embodiment, if enough information is available to the third intelligent agent, the agent may automatically generate optimal patient management plan including patient logistics (length-of-stay management, bed management, nursing management, etc.). For example, in one embodiment, the third intelligent agent may modify one or more pre-generated patient management plans stored in the Common Knowledge Database 220 to tailor it to the patient. Aside from patient management plans, in some embodiments, the third intelligent agent is further trained to design an optimal drug therapy for the patent. Again, information in the Common Knowledge Database 220 may be utilized to design each drug therapy plan based, for example, on drug therapy plans previously used for patients having similar characteristics to the patient currently being analyzed.

In some embodiments, any information acquired or derived during execution of the method 300 (including, without limitation, reports on the agents' actions and patient outcome) may be anonymized and stored in the Common Knowledge Database 220 for later use in training the intelligent agents (e.g., with simulated clinical studies).

To illustrate the utility of the multi-agent system 200 and method 300 discussed above, the following paragraphs describe an example of applying the techniques described herein to the management of coronary artery disease (CAD) patients. Upon admission, the CAD patient can present with symptoms including chest pain, shortness of breath, weakness, dizziness etc. Clinical history can include the same symptoms. Based on current clinical guidelines and clinical presentation, a first intelligent agent (IA1) would stratify the patient population, referring different patients to different (invasive or non-invasive) tests for myocardial ischemia. In the case of patients presenting with pre-test high probability of obstructive CAD, they would be directly referred to the catheterization lab for immediate treatment.

The wealth of available tests include invasive testing (e.g., coronary angiography, with invasive measurement of FFR), non-invasive testing (e.g., stress echocardiography, stress ECG, perfusion imaging, computed tomography). A stable patient meeting proper eligibility criteria could be for instance referred to coronary computed tomography angiography (CTA), a modality featuring excellent sensitivity and negative predictive value. The imaging acquisition protocol could also be determined by the intelligent agent, to optimize image quality for the intended application (detection of obstructive CAD).

In another embodiment, an additional dedicated intelligent agent could focus specifically on selecting the imaging protocol: for instance, determining how much contrast agent to infuse for the angiographic image acquisition, how much beta blocker to administer to control heart rate, what parameters to set on the imaging scanner (e.g., what reconstruction kernel), the amount of radiation dose, the dimension of the field of view (whole chest or only heart), the number of phases to be reconstructed (e.g., only the best phase in the diastolic window, or all frames to determine cardiac function, etc.)

Given the acquired medical images, a second intelligent agent (IA2) could apply one or more of a number of image processing techniques, including automatic segmentation of the coronary arterial tree, automatic detection and grading of coronary lesions, automatic quantification of regional myocardial perfusion. A report could be automatically generated by the intelligent agent describing all diagnostic findings.

A third intelligent agent (IA3) could interpret the report and map it back to the original clinical question. If the findings support a definitive assessment of the status of the patient, the intelligent agent could propose a diagnosis. The agent could also provide an estimate of the uncertainty in the proposed diagnosis, for instance based on the analysis of patient data in the common knowledge database. In case the findings of the report do not support a definite diagnosis, the intelligent agent could invoke the agents at the previous stages in the workflow to define an alternative management plan.

An example of bifurcation in the management plan is the case in which coronary CTA testing is positive for CAD. Due to the relatively low specificity of the test, no definite assessment of the patient status can be done based on this result. IA1 could be invoked, providing as additional input the results of non-invasive testing. IA1 would then order more testing to improve the confidence in the final diagnosis. One option would be to perform invasive testing (e.g., coronary angiography); in which case, new imaging data would be presented to IA2, and correspondingly new image processing would be applied.

A different option would be to further process existing CTA images, applying physiological modeling techniques to estimate the severity of coronary lesions. This technology has been proven to increase the specificity of CTA for the assessment of CAD. In this case, IA2 could invoke a fourth intelligent agent (IA4) for setting up and running the physiological model. The application of physiological modeling to improve specificity and diagnostic accuracy of non-invasive diagnostic imaging tests are generally understood in the art and can be readily incorporated into the techniques described herein.

Figure 4:
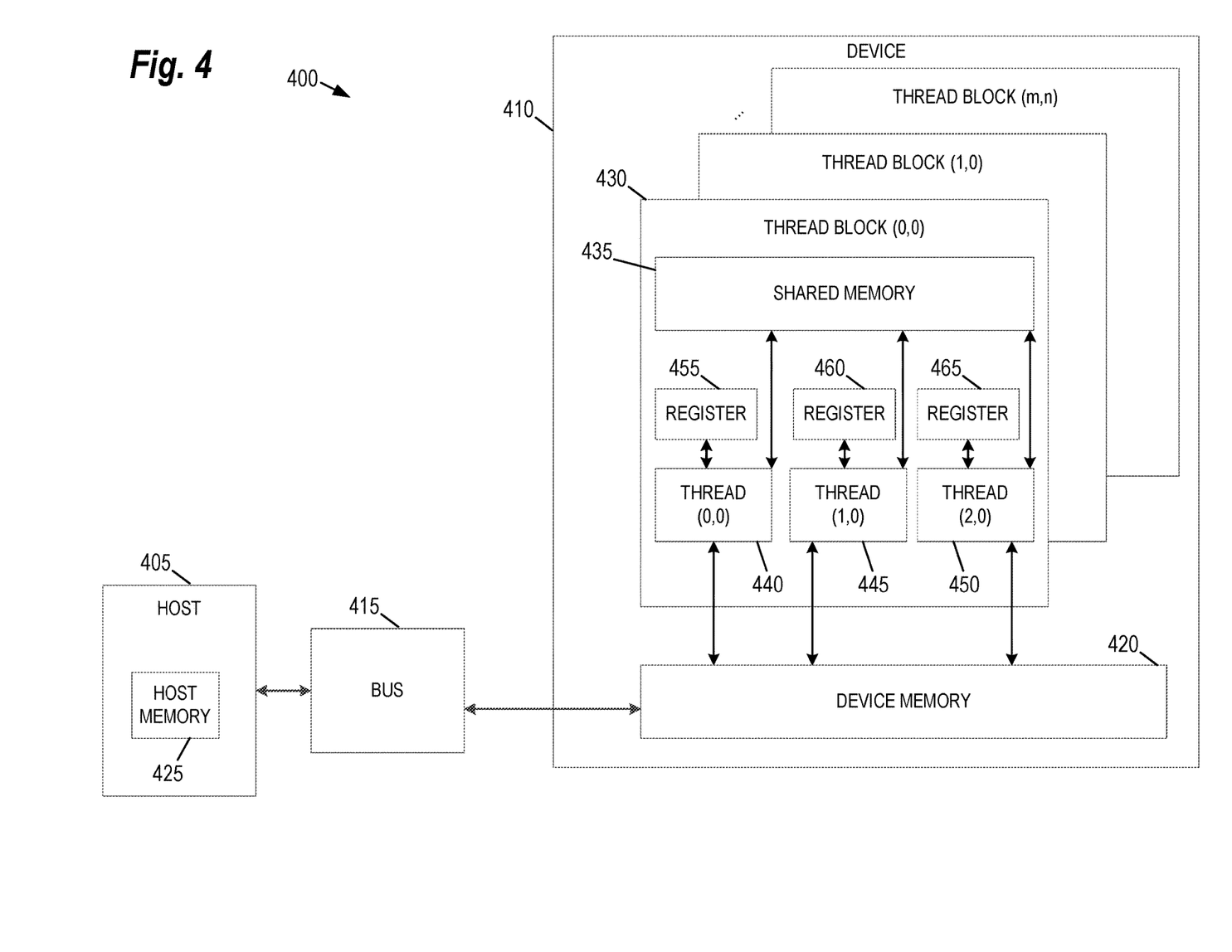
FIG. 4 illustrates an exemplary computing environment within which embodiments of the invention may be implemented.

FIG. 4 provides an example of a parallel processing platform 400 that may be utilized to implement the machine learning models and other aspects of the various processes discussed herein. This platform 400 may be used in embodiments of the present invention where NVIDIA CUDA™ (or a similar parallel computing platform) is used. The architecture includes a host computing unit ("host") 405 and a graphics processing unit (GPU) device ("device") 410 connected via a bus 415 (e.g., a PCIe bus). The host 405 includes the central processing unit, or "CPU" (not shown in FIG. 4), and host memory 425 accessible to the CPU. The device 410 includes the graphics processing unit (GPU) and its associated memory 420, referred to herein as device memory. The device memory 420 may include various types of memory, each optimized for different memory usages. For example, in some embodiments, the device memory includes global memory, constant memory, and texture memory.

Parallel portions of a big data platform and/or big simulation platform may be executed on the platform 400 as "device kernels" or simply "kernels." A kernel comprises parameterized code configured to perform a particular function. The parallel computing platform is configured to execute these kernels in an optimal manner across the platform 400 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by a grid of thread blocks (described in greater detail below). Using concurrent kernel execution, streams, and synchronization with lightweight events, the platform 400 of FIG. 4 (or similar architectures) may be used to parallelize portions of the model based operations performed in training or utilizing the smart editing processes discussed herein. For example, in embodiments where a convolutional neural network is used as the machine learning model, the platform 400 can be used to perform operations such as forward and backward convolution, pooling, normalization, etc. Additionally, the parallel processing platform 400 may be used to execute multiple instances of a machine learning model in parallel. For example, in some embodiments, various datasets in the common knowledge database are evaluated in parallel using multiple instances of an intelligent agent executing a machine learning algorithm.

The device 410 includes one or more thread blocks 430 which represent the computation unit of the device 410. The term thread block refers to a group of threads that can cooperate via shared memory and synchronize their execution to coordinate memory accesses. For example, in FIG. 4, threads 440, 445 and 450 operate in thread block 430 and access shared memory 435. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 4, the thread blocks 430 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints.

Continuing with reference to FIG. 4, registers 455, 460, and 465 represent the fast memory available to thread block 430. Each register is only accessible by a single thread. Thus, for example, register 455 may only be accessed by thread 440. Conversely, shared memory is allocated per thread block, so all threads in the block have access to the same shared memory. Thus, shared memory 435 is designed to be accessed, in parallel, by each thread 440, 445, and 450 in thread block 430. Threads can access data in shared memory 435 loaded from device memory 420 by other threads within the same thread block (e.g., thread block 430). The device memory 420 is accessed by all blocks of the grid and may be implemented using, for example, Dynamic Random-Access Memory (DRAM).

Each thread can have one or more levels of memory access. For example, in the platform 400 of FIG. 4, each thread may have three levels of memory access. First, each thread 440, 445, 450, can read and write to its corresponding registers 455, 460, and 465. Registers provide the fastest memory access to threads because there are no synchronization issues and the register is generally located close to a multiprocessor executing the thread. Second, each thread 440, 445, 450 in thread block 430, may read and write data to the shared memory 435 corresponding to that block 430. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 410 to read and/or write to the device memory. Device memory requires the longest time to access because access must be synchronized across the thread blocks operating on the device. Thus, in some embodiments, each brain imaging dataset can be divided into segments using data locality techniques generally known in the art. Then, each segment can be processed in parallel using register memory, with shared and device memory only being used as necessary to combine the results to provide the results for the complete dataset.

The embodiments of the present disclosure may be implemented with any combination of hardware and software. For example, aside from parallel processing architecture presented in FIG. 4, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) unless the element is expressly recited using the phrase "means for."

The invention claimed is:

1. A computer-implemented method for executing patient management workflows, the method comprising:
receiving one or more electronic medical records (EMRs) including a pre-test patient data of clinically relevant information related to a particular patient;
parsing the EMRs and extracting the pre-test patient data from the EMRs to obtain a pre-test dataset;
retrieving patient data of a plurality of patients from a common knowledge database, wherein the common knowledge database includes patient symptoms, clinical history, medical data, medical imaging, background knowledge from medical literature, clinical guidelines, and use criteria;
training a first intelligent agent including a first neural network, a second intelligent agent including a second neural network, and a third intelligent agent including a third neural network using the common knowledge database;
using the trained first intelligent agent to identify a diagnostic imaging test for the particular patient based on the pre-test dataset, and identify an optimal imaging protocol for performing the diagnostic imaging test, wherein the optimal imaging protocol includes an amount of contrast agent, an amount of beta blocker, an amount of radiation dose, a dimension of a field of view, and a number of phases to be reconstructed;

following performance of the diagnostic imaging test, using the trained second intelligent agent to (i) select an imaging processing technique to be applied to imaging data collected from the diagnostic imaging test to obtain a diagnostic marker and (ii) automatically apply the imaging processing technique to the imaging data to obtain the diagnostic marker, wherein the imaging processing technique includes segmentation of the imaging data and extraction of geometry features of the particular patient for physiological modeling, wherein each segment is processed in parallel using a plurality of register memories;

following application of the imaging processing technique to the imaging data collected from the diagnostic imaging test, using the trained third intelligent agent to generate an optimal patient management plan, wherein generating the optimal patient management plan comprises:
retrieving, from the common knowledge database, a pre-generated patient management plan,
receiving a constraint, wherein a constraint is an item that is not available at a location where the patient management plan will be performed, and
modifying the pre-generated patient management plan based on the pre-test dataset, the imaging data collected from the diagnostic imaging test, the diagnostic marker, the constraint to generate the optimal patient management plan;

continuously updating the common knowledge database with the pre-test dataset, the imaging data collected from the diagnostic imaging test, and the diagnostic marker of the particular patient; and retraining the first intelligent agent, the second intelligent agent, and the third intelligent agent using the updated common knowledge database.

2. The method of claim 1, wherein the pre-test dataset of clinically relevant information related to the patient is acquired by:
receiving one or more electronic medical records comprising the clinically relevant information; and
automatically extracting the clinically relevant information from the one or more electronic medical records to yield the pre-test dataset.

3. The method of claim 1, further comprising:
wherein the first intelligent agent identifies the diagnostic imaging test for the patient based on the pre-test dataset and the patient data.

4. The method of claim 1, further comprising:
wherein the second intelligent agent selects the imaging processing technique to be applied to data collected from the diagnostic imaging test based on the patient data.

5. The method of claim 1, wherein the imaging processing technique comprises one or more of segmentation of a vascular tree, detection of vascular lesions, classification of detected lesions into clinical sub-types, or extraction of geometry features for physiological modeling.

6. The method of claim 1, wherein the patient management plan comprises patient logistics information corresponding to a medical facility.

7. The method of claim 1, further comprising training the plurality of intelligent agents by curriculum training to first learn a first set of actions maximizing a positive outcome for patient irrespective of cost and time efficiency, and then learn a second set of actions improving the cost and time efficiency.

8. The method of claim 1, further comprising training the first intelligent agent, the second intelligent agent, and the third intelligent agent using ground truth including a human expert's knowledge.

9. The method of claim 1, further comprising:
using the third intelligent agent to generate an optimal drug therapy plan based on the pre-test dataset, the data collected from the diagnostic imaging test, and the diagnostic marker.

10. A system for executing patient management workflows, the system comprising:
a common knowledge database comprising clinically relevant information related to a population of patients;
a first intelligent agent including a first neural network configured to identify a diagnostic imaging test for the patient based on one or more of (a) a pre-test dataset of clinically relevant information related to a patient and (b) the clinically relevant information, and identify an optimal imaging protocol for performing the diagnostic imaging test, wherein the optimal imaging protocol includes an amount of contrast agent, an amount of beta blocker, an amount of radiation dose, a dimension of a field of view, and a number of phases to be reconstructed;
a second intelligent agent including a second neural network configured to:
select an imaging processing technique to be applied to imaging data collected from the diagnostic imaging test to obtain a diagnostic marker based on one or more of (a) the pre-test dataset and (b) the clinically relevant information, wherein the imaging processing technique includes segmentation of the imaging data and extraction of geometry features of the patient for physiological modeling, wherein each segment is processed in parallel using a plurality of register memories;
following selection, automatically perform the imaging processing technique to obtain the diagnostic marker;
a third intelligent agent including a third neural network configured to generate an optimal patient management plan, wherein generating the optimal patient management plan comprises:
retrieving, from the common knowledge database, a pre-generated patient management plan,
receiving a constraint, wherein a constraint is an item that is not available at a location where the patient management plan will be performed, and
modifying the pre-generated patient management plan based on one or more of (a) the pre-test dataset, (b) the clinically relevant information, (c) the imaging data collected from the diagnostic imaging test, (d) the diagnostic marker, and (e) the constraint to generate the optimal patient management plan; and
a plurality of computers configured to execute the first intelligent agent, the second intelligent agent, and the third intelligent agent;
the intelligent agents communicate with one another using one or more application programming interfaces;
wherein the first intelligent agent, the second intelligent agent, and the third intelligent agent were trained using the common knowledge database comprising patient symptoms, clinical history, medical data, medical imaging, background knowledge from medical literature, clinical guidelines, and use criteria; wherein the common knowledge database is continuously updated with the pre-test dataset, the imaging data collected from the diagnostic imaging test, and the diagnostic marker of the patient; and the first intelligent agent, the second intelligent agent, and the third intelligent agent are retrained using the updated common knowledge database.

11. The system of claim 10, further comprising a pre-test interface configured to:
receive one or more electronic medical records comprising the clinically relevant information; and
automatically extract the clinically relevant information from the one or more electronic medical records to yield the pre-test dataset.

12. The system of claim 10, wherein the imaging processing technique comprises one or more of segmentation of a vascular tree, detection of vascular lesions, or extraction of geometry features for physiological modeling.

13. The system of claim 10, wherein the patient management plan comprises patient logistics information corresponding to a medical facility.

14. The system of claim 10, wherein the third intelligent agent is further configured to generate an optimal drug therapy plan based on one or more of (a) the pre-test dataset, (b) the clinically relevant information, (c) the data collected from the diagnostic imaging test, and (d) the diagnostic marker.

15. A multi-agent system for executing patient management workflows, the system comprising:
a common knowledge database comprising clinically relevant information related to a population of patients;
a computer executing a plurality of intelligent agents, wherein each intelligent agent includes a neural network, the plurality of intelligent agents are configured to:
identify a diagnostic imaging test for the patient based on one or more of (a) a pre-test dataset of clinically relevant information related to a patient and (b) the clinically relevant information;
identify an optimal imaging protocol for performing the diagnostic imaging test, wherein the optimal imaging protocol includes an amount of contrast agent, an amount of beta blocker, an amount of radiation dose, a dimension of a field of view, and a number of phases to be reconstructed;
select an imaging processing technique to be applied to imaging data collected from the diagnostic imaging test to obtain a diagnostic marker based on one or more of (a) the pre-test dataset and (b) the clinically relevant information; wherein the imaging processing technique includes segmentation of the imaging data and extraction of geometry features of the patient for physiological modeling, wherein each segment is processed in parallel using a plurality of register memories;
automatically apply the imaging processing technique to the imaging data;
generate an optimal patient management plan wherein generating the optimal patient management plan comprises:
retrieving, from the common knowledge database, a pre-generated patient management plan,
receiving a constraint, wherein a constraint is an item that is not available at a location where the patient management plan will be performed, and
modifying the pre-generated patient management plan based on one or more of (a) the pre-test dataset, (b) the clinically relevant information, (c) the imaging data collected from the diagnostic imaging test, (d) the diagnostic marker, and (e) the constraint to generate the optimal patient management plan;
a facility; and
a graphical user interface (GUI) configured to present the optimal patient management plan,
the plurality of intelligent agents communicate with one another using one or more application programming interfaces,
wherein the plurality of intelligent agents were trained using the common knowledge database comprising patient symptoms, clinical history, medical data, medical imaging, background knowledge from medical literature, clinical guidelines, and use criteria; wherein the common knowledge database is continuously updated with the pre-test dataset, the imaging data collected from the diagnostic imaging test, and the diagnostic marker of the patient; and the plurality of intelligent agents are retrained using the updated common knowledge database.

* * * * *